(12) United States Patent
Davison

(10) Patent No.: US 10,576,236 B2
(45) Date of Patent: Mar. 3, 2020

(54) OXYGEN DELIVERY DEVICE

(71) Applicant: Arthur Davison, Brighton, CO (US)

(72) Inventor: Arthur Davison, Brighton, CO (US)

(*) Notice: Subject to any disclaimer, the term of this patent is extended or adjusted under 35 U.S.C. 154(b) by 309 days.

(21) Appl. No.: 15/628,014

(22) Filed: Jun. 20, 2017

(65) Prior Publication Data

US 2018/0361103 A1 Dec. 20, 2018

(51) Int. Cl.
*A61M 16/10* (2006.01)
*A61M 16/06* (2006.01)
(Continued)

(52) U.S. Cl.
CPC ...... *A61M 16/101* (2014.02); *A61M 16/0672* (2014.02); *A61M 16/0875* (2013.01); *A61M 2202/0208* (2013.01); *A61M 2209/08* (2013.01); *A61M 2209/084* (2013.01); *C01B 13/02* (2013.01)

(58) Field of Classification Search
CPC .......... A61M 16/0666; A61M 16/0672; A61M 16/0683; A61M 16/08; A61M 16/0875; A61M 16/10; A61M 16/101; A61M 2039/087; A61M 2202/0007; A61M 2202/02; A61M 2202/0208; A61M 2202/0283; A61M 2202/03; A61M 2209/00; A61M 2209/06; A61M 2209/08; A61M 2209/084; A61M 2209/088; A61M 39/08; A62B 9/00; B65H 2701/33; B65H 75/265; B65H 75/38; B65H 75/40; B65H 75/406; B65H 75/4402; B65H 75/4407; B65H 75/4431; B65H 75/4434; B65H 75/4449; B65H 75/446; B65H 75/4463; B65H 75/4471; B65H 75/4478; B65H 75/4484; B65H 75/4486; B65H 75/4492; B65H 75/48; B65H 75/486; C01B 13/02; F16L 3/012; Y10T 137/0402; Y10T 137/0441; Y10T 137/6918; Y10T 137/6929; Y10T 137/6932; Y10T 137/6936; Y10T 137/694; Y10T 137/6943; Y10T 137/6954; Y10T 137/6962; Y10T 137/8158
See application file for complete search history.

(56) References Cited

U.S. PATENT DOCUMENTS 3,800,819 A * 4/1974 McKee ................. A61M 16/00
137/343
4,257,415 A * 3/1981 Rubin ............... A61M 16/0057
128/200.21
(Continued)

*Primary Examiner* — Annette Dixon

(57) ABSTRACT

An oxygen delivery device for providing oxygen to a user through a retractable tube includes a first housing. An oxygen supplier, such as an oxygen concentrator, is positioned in the first housing. A reel, which is spring-loaded, is rotationally coupled to and positioned in the first housing. A door is positioned in and is hingedly coupled to the first housing proximate to the reel to allow access to the reel. A tube is coiledly positioned around the reel. The tube has a first end that is fluidically coupled to the oxygen supplier. The tube is positioned around the reel such that a second end of the tube is configured to be selectively and reversibly extended from the first housing through a hole that is positioned through the door. The second end of the tube is positioned to couple to an oxygen supply interface, such as a cannula.

16 Claims, 5 Drawing Sheets

(51) Int. Cl.
*A61M 16/08* (2006.01)
*C01B 13/02* (2006.01)

(56) References Cited

U.S. PATENT DOCUMENTS

| | | | | |
|---|---|---|---|---|
| 5,144,945 | A * | 9/1992 | Nishino | A62B 7/00 |
| | | | | 128/204.15 |
| 5,431,263 | A * | 7/1995 | Nordstrom | A45C 5/14 |
| | | | | 190/18 A |
| 6,065,490 | A | 5/2000 | Falcone, Jr. | |
| 7,350,520 | B1 * | 4/2008 | Richard-Bey | A61M 11/06 |
| | | | | 128/200.14 |
| D595,121 | S | 6/2009 | Murphy | |
| 8,707,950 | B1 * | 4/2014 | Rubin | A61M 16/06 |
| | | | | 128/202.27 |
| 9,403,662 | B1 | 8/2016 | Evans et al. | |
| 2007/0045152 | A1 * | 3/2007 | Kwok | A61M 16/00 |
| | | | | 206/733 |
| 2009/0205991 | A1 | 8/2009 | Lill | |
| 2011/0017856 | A1 | 1/2011 | Penn | |
| 2015/0069164 | A1 | 3/2015 | Moore | |
| 2016/0060075 | A1 | 3/2016 | Slowik | |
| 2016/0310691 | A1 * | 10/2016 | Bath | A61M 16/16 |

* cited by examiner

OXYGEN DELIVERY DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed under 37 CFR 1.97 and 1.98

The disclosure and prior art relates to oxygen delivery devices and more particularly pertains to a new oxygen delivery device for providing oxygen to a user through a retractable tube.

BRIEF SUMMARY OF THE INVENTION

An embodiment of the disclosure meets the needs presented above by generally comprising a first housing. An oxygen supplier, such as an oxygen concentrator, is positioned in the first housing. A reel, which is spring-loaded, is rotationally coupled to and positioned in the first housing. A door is positioned in and is hingedly coupled to the first housing proximate to the reel to allow access to the reel. A tube is coiledly positioned around the reel. The tube has a first end that is fluidically coupled to the oxygen supplier. The tube is positioned around the reel such that a second end of the tube is configured to be selectively and reversibly extended from the first housing through a hole that is positioned through the door. The second end of the tube is positioned to couple to an oxygen supply interface, such as a cannula.

There has thus been outlined, rather broadly, the more important features of the disclosure in order that the detailed description thereof that follows may be better understood, and in order that the present contribution to the art may be better appreciated.

There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
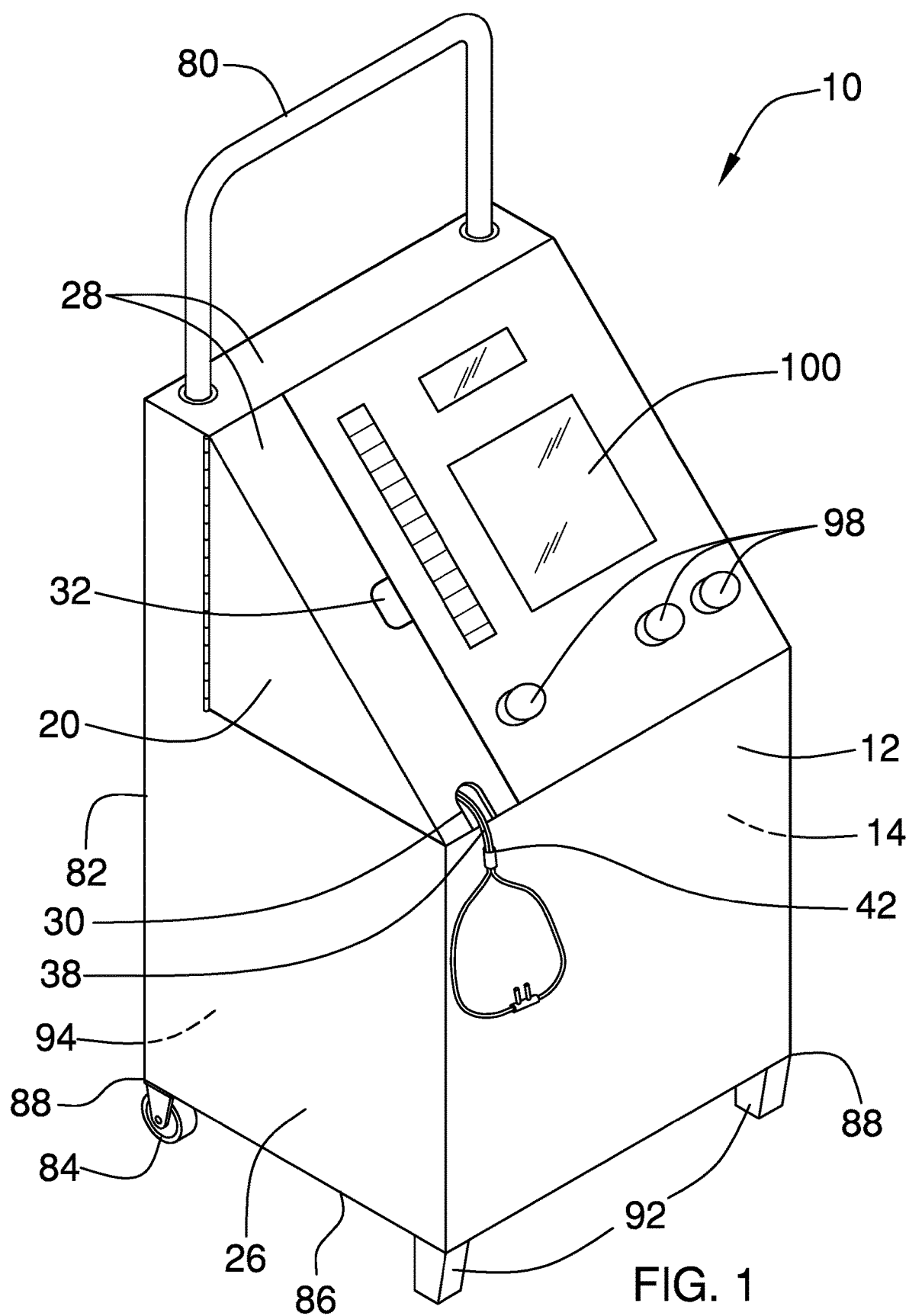
FIG. 1 is an isometric perspective view of an oxygen delivery device according to an embodiment of the disclosure.
Figure 2:
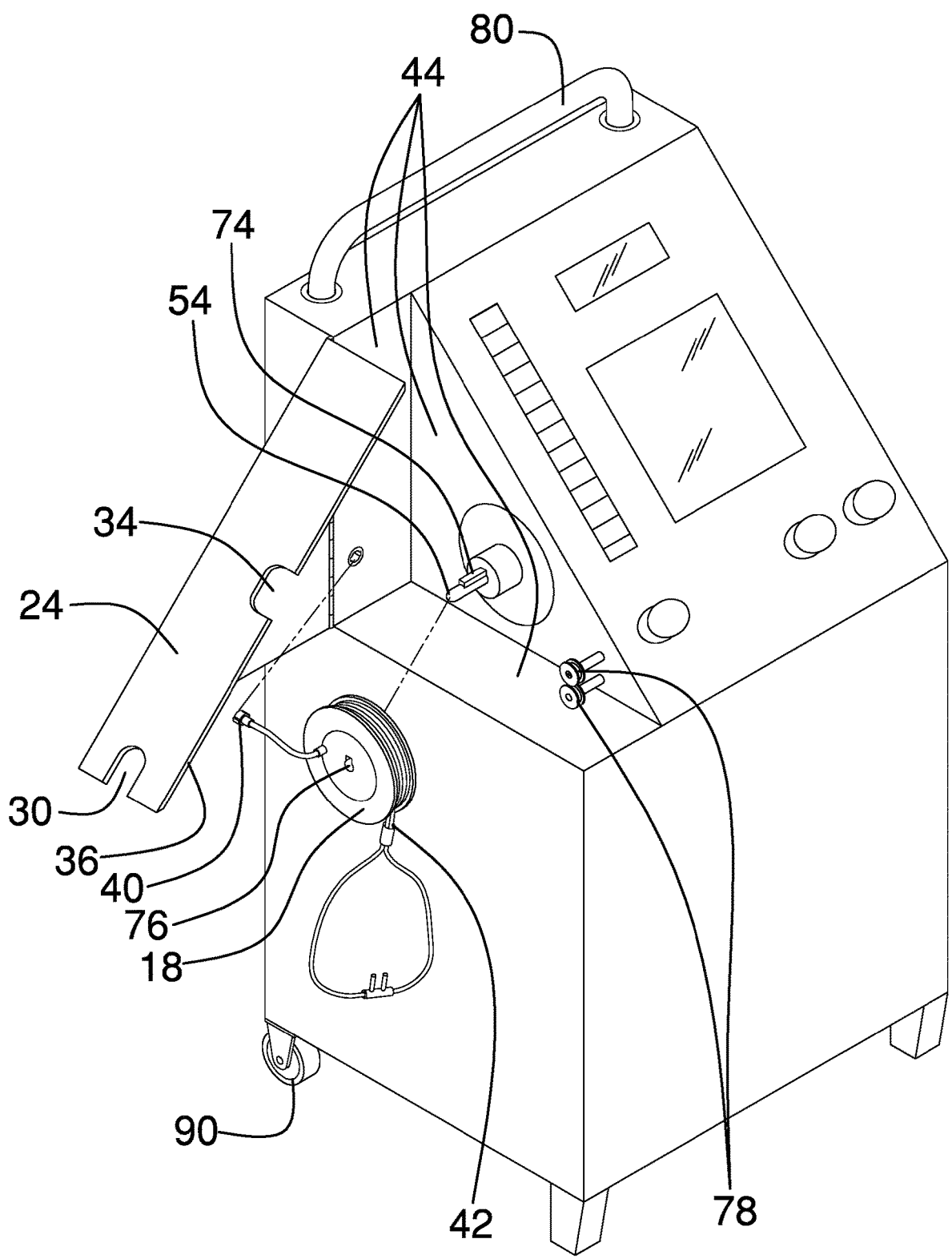
FIG. 2 is an isometric perspective view of an embodiment of the disclosure.
Figure 3:
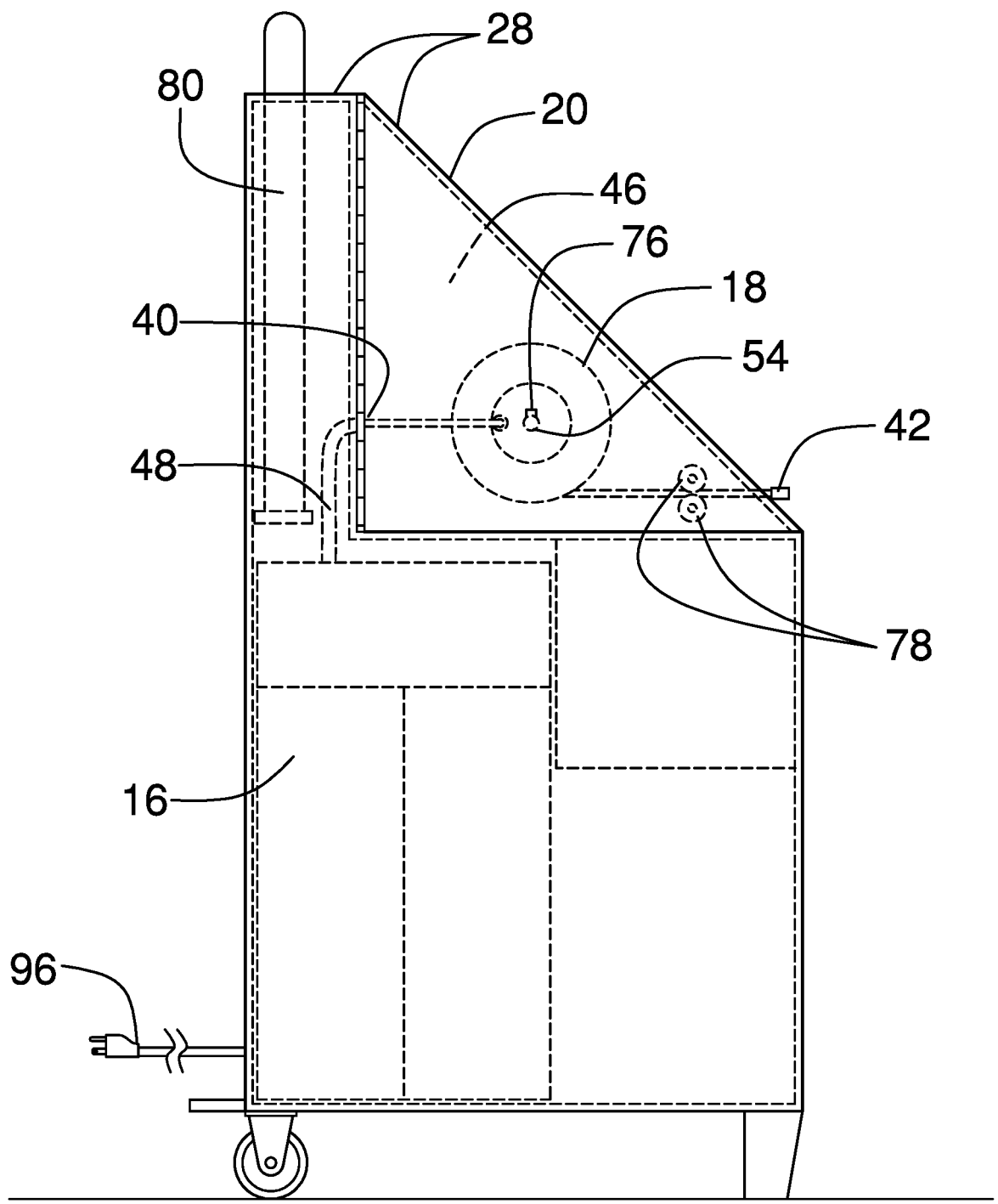
FIG. 3 is a side view of an embodiment of the disclosure.
Figure 4:
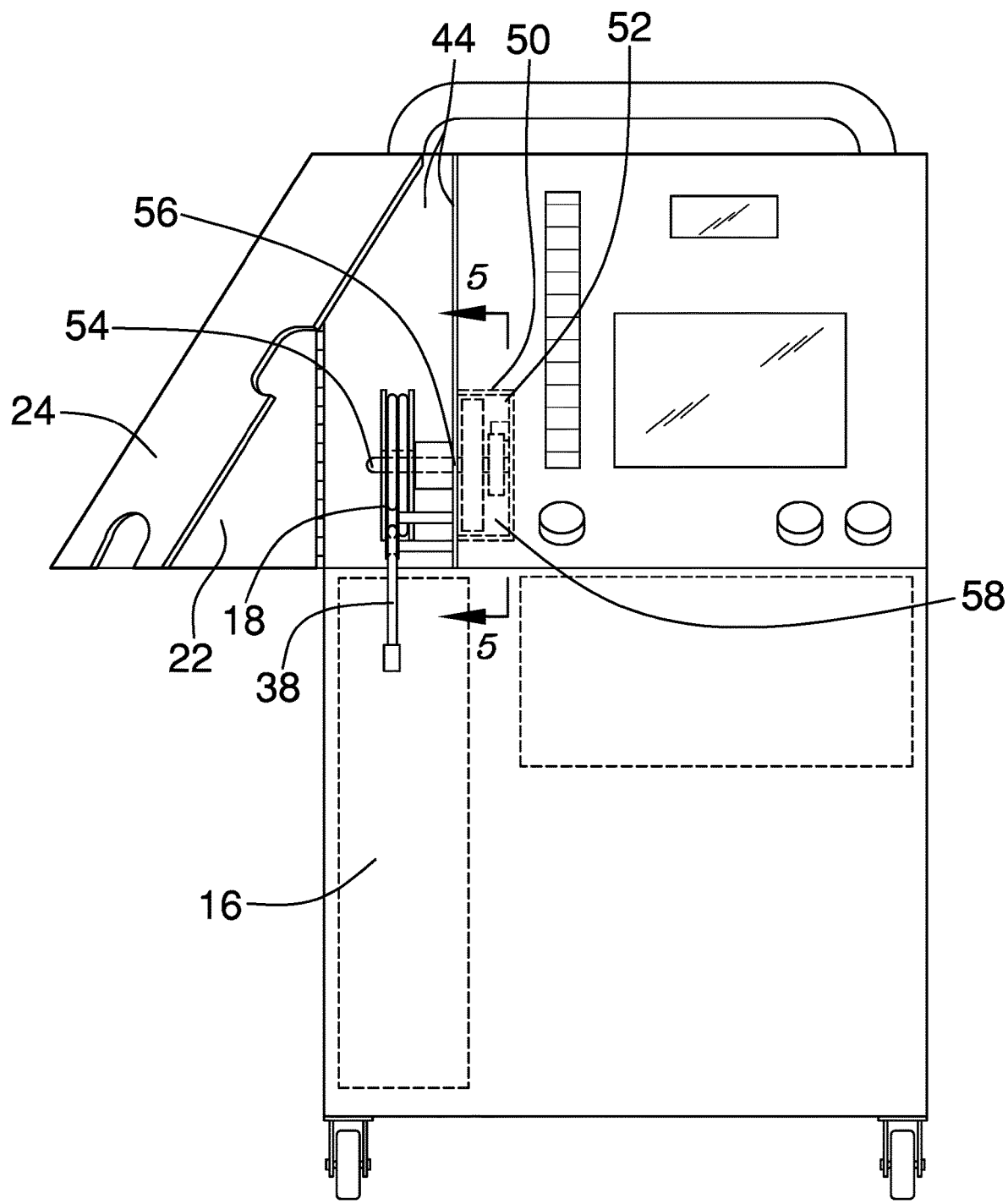
FIG. 4 is a front view of an embodiment of the disclosure.
Figure 5:
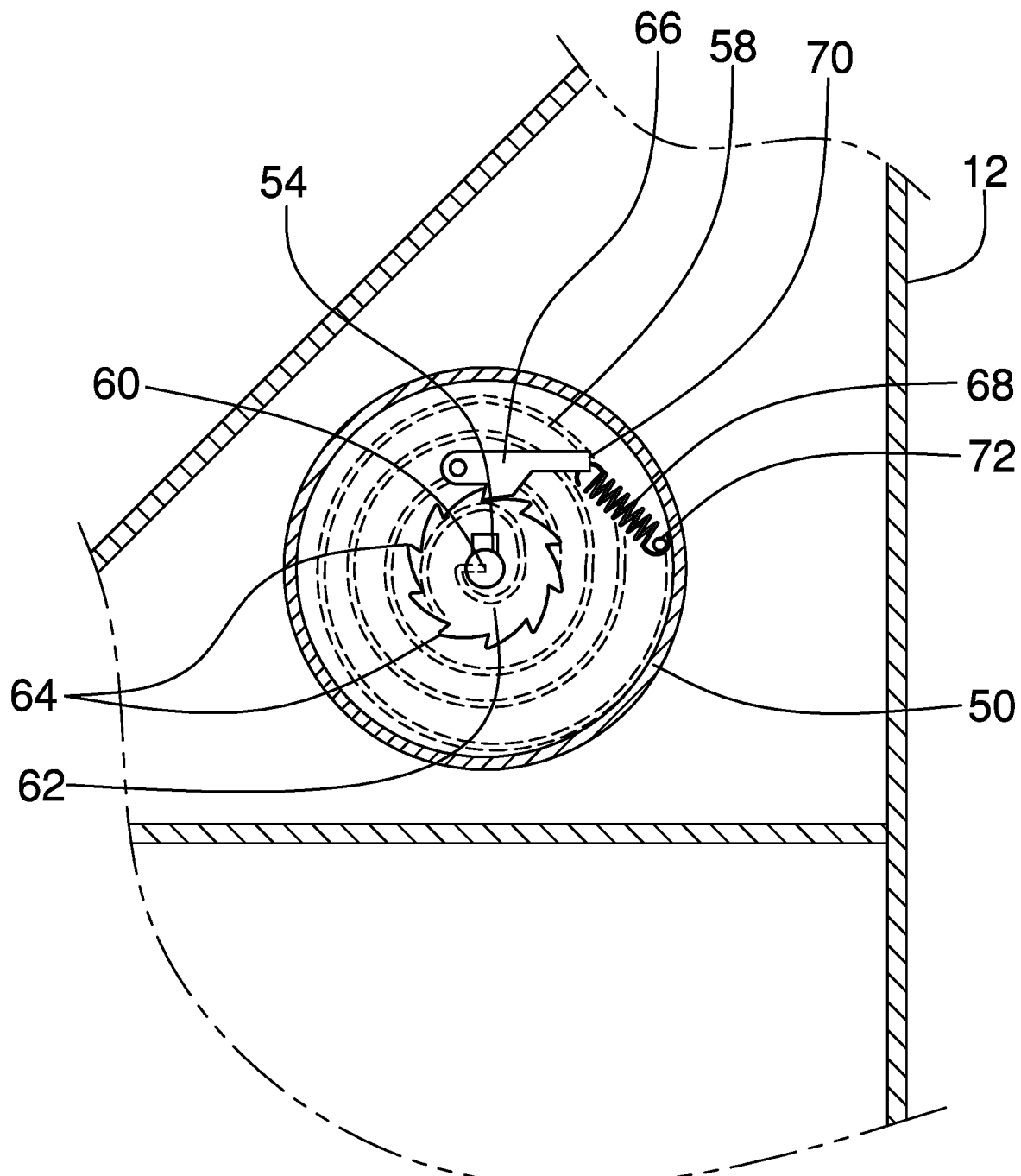
FIG. 5 is a cross-sectional view of an embodiment of the disclosure.

With reference now to the drawings, and in particular to FIGS. 1 through 5 thereof, a new oxygen delivery device embodying the principles and concepts of an embodiment of the disclosure and generally designated by the reference numeral 10 will be described.

As best illustrated in FIGS. 1 through 5, the oxygen delivery device 10 generally comprises a first housing 12 that defines an internal space 14. An oxygen supplier 16, such as an oxygen concentrator, is positioned in the internal space 14. A reel 18 is rotationally coupled to the first housing 12 and is positioned in the internal space 14. The reel 18 is spring-loaded.

A door 20 is positioned in and is hingedly coupled to the first housing 12 proximate to the reel 18. The door 20 is configured to be opened to allow access to the reel 18. In one embodiment, the door 20 comprises a first section 22 and a second section 24. The first section 22 is positioned in and is hingedly coupled to a respective side 26 of the first housing 12. The second section 24 is coupled to and extends perpendicularly from the first section 22 into a top 28 of the first housing 12. A hole 30 is positioned through the door 20.

A grasp 32 is coupled to the door 20. The grasp 32 is configured to be grasped is a hand of a user to open and close the door 20. In one embodiment, the grasp 32 comprises a cutout 34 that is positioned through the door 20 adjacent to an edge 36 of the door 20.

A tube 38 is coiledly positioned around the reel 18. The tube 38 has a first end 40 that is fluidically coupled to the oxygen supplier 16. The tube 38 is positioned around the reel 18 such that a second end 42 of the tube 38 is configured to be selectively and reversibly extended from the first housing 12 through the hole 30. The second end 42 of the tube 38 is positioned to couple to an oxygen supply interface, such as a mask and a cannula.

A plurality of panels 44 is coupled to the first housing 12 and is positioned in the internal space 14 to define a compartment 46. The door 20 is configured to be opened to allow access to the compartment 46.

A pipe 48 is fluidically coupled to the oxygen supplier 16. The pipe 48 extends from the oxygen supplier 16 to the compartment 46. The pipe 48 is positioned to fluidically couple the tube 38 to the oxygen supplier 16.

A second housing 50 is coupled to a respective panel 44 and is positioned in the internal space 14. The second housing 50 and the respective panel 44 define an interior space 52.

A shaft 54 is rotationally coupled to the second housing 50. The shaft 54 extends from the second housing 50 through a penetration 56 in the respective panel 44 into the compartment 46. The shaft 54 is complementary to the reel 18 and is positioned to couple to the reel 18.

A first spring 58 is positioned in the interior space 52. The first spring 58 is clock-type. The first spring 58 is coupled by an inner end 60 to the shaft 54. The first spring 58 is configured to be compressed as the tube 38 is extended from the compartment 46. The first spring 58 is positioned to compel rotation of the reel 18 coincident with the shaft 54 to retract the tube 38 into the compartment 46.

In one embodiment, a ratchet wheel 62 is coupled to the shaft 54 and is positioned in the interior space 52. The ratchet wheel 62 comprises a plurality of teeth 64. A pawl 66 is hingedly coupled to the second housing 50 and is positioned in the interior space 52. The pawl 66 is operationally coupled to the ratchet wheel 62. A second spring 68 is coupled to and extends between an endpoint 70 of the pawl 66 and an outer endpoint 72 of the first spring 58. The second spring 68 is extension-type. The second spring 68 is configured to extend coincident with compression of the first spring 58 and extension of the tube 38 from the compartment 46. The second spring 68 is positioned to partially rebound to compel the pawl 66 to couple to the ratchet wheel 62. The tube 38 is fixedly extended from the compartment 46. The tube 38 is configured to be grasped and extended from the compartment 46 so that the pawl 66 is compelled to decouple from the ratchet wheel 62. The first spring 58 is positioned to compel rotation of the reel 18 coincident with the shaft 54 to retract the tube 38 into the compartment 46, In another embodiment, a bar 74 is coupled to the shaft 54. The bar 74 is positioned longitudinally on the shaft 54 within the compartment 46. A channel 76 is axially positioned through the reel 18. The channel 76 is complementary to shaft 54 and the bar 74. The channel 76 is positioned to insert the bar 74 and the shaft 54 to couple the reel 18 to the shaft 54.

In yet another embodiment, a pair of pulleys 78 is rotationally coupled to the respective panel 44. The pulleys 78 are positioned in the compartment 46 proximate to the hole 30 when the door 20 is closed. The pulleys 78 are positioned to rotationally couple to the tube 38 to guide the tube 38 as the tube 38 is selectively extended from and retracted into the compartment 46.

A handle 80 is coupled to and selectively extensible from the first housing 12. The handle 80 is positioned on the top 28 of the first housing 12 proximate to a back 82 of the first housing 12.

A pair of rollers 84 is coupled to and extends from a bottom 86 of the first housing 12. The rollers 84 are positioned proximate to the back 82 of the first housing 12. Each roller 84 is positioned proximate to a respective corner 88 of the bottom 86. In one embodiment, the rollers 84 comprise castors 90.

A pair of legs 92 is coupled to and extends from the bottom 86 of the first housing 12. The legs 92 are positioned proximate to the back 82 of the first housing 12. Each leg 92 is positioned proximate to a respective corner 88 of the bottom 86. In one embodiment, the legs 92 are dimensionally taller than the rollers 84 so that the first housing 12 is tilted.

A power module 94 is coupled to the first housing 12 and is positioned in the internal space 14. The power module 94 is operationally coupled to the oxygen supplier 16. In one embodiment, the power module 94 comprises a cord 96. The cord 96 is configured to couple to a source of alternating current. In another embodiment, the cord 96 is retractable into the internal space 14.

A control panel 98 is coupled to the top 28 of the first housing 12. The control panel 98 is operationally coupled to the power module 94 and the oxygen supplier 16. The control panel 98 is configured to enter commands to control a flow rate of oxygen from the oxygen supplier 16 through the tube 38.

A display 100 is coupled to the top 28 of the first housing 12. The display 100 is operationally coupled to the power module 94 and the control panel 98. The display 100 is configured to present to the user the flow rate of the oxygen from the oxygen supplier 16 through the tube 38.

In use, the door 20 is configured to be opened to allow access to the compartment 46 to install and replace the reel 18. The pipe 48 that is positioned on the oxygen supplier 16 is positioned to fluidically couple the tube 38 to the oxygen supplier 16. The pulleys 78 are positioned to rotationally couple to the tube 38 to guide the tube 38 as the tube 38 is selectively extended from and retracted into the compartment 46. The second spring 68 that is positioned on the pawl 66 is configured to extend coincident with compression of the first spring 58 and extension of the tube 38 from the compartment 46. The second spring 68 is positioned to partially rebound to compel the pawl 66 to couple to the ratchet wheel 62. The tube 38 is fixedly extended from the compartment 46. The second end 42 of the tube 38 is positioned to couple to the oxygen supply interface, such as the mask and the cannula. The tube 38 is configured to be grasped and extended from the compartment 46. The pawl 66 is compelled to decouple from the ratchet wheel 62 so that the first spring 58 is positioned to compel rotation of the reel 18 coincident with the shaft 54 to retract the tube 38 into the compartment 46. The control panel 98 is configured to enter the commands to control the flow rate of the oxygen from the oxygen supplier 16 through the tube 38. The display 100 is configured to present to the user the flow rate of the oxygen from the oxygen supplier 16 through the tube 38.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An oxygen delivery device comprising:
a first housing defining an internal space;
an oxygen supplier positioned in said internal space;
a reel rotationally coupled to said first housing and positioned in said internal space, said reel being spring-loaded;
a door positioned in and hingedly coupled to said first housing proximate to said reel;
a hole positioned through said door;
a tube coiledly positioned around said reel, said tube having a first end fluidically coupled to said oxygen supplier;
wherein said door is positioned in said first housing such that said door is configured for opening for accessing said reel, wherein said tube is positioned around said reel such that a second end of said tube is configured for selectively reversibly extending from said first housing through said hole positioning said second end for coupling to an oxygen supply interface
a plurality of panels coupled to said first housing and positioned in said internal space defining a compartment, wherein said door is positioned in said first housing such that said door is configured for opening for accessing said compartment;
a second housing coupled to a respective said panel and positioned in said internal space, said second housing and said respective said panel defining an interior space;
a shaft rotationally coupled to said second housing, said shaft extending from said second housing through a penetration in said respective said panel into said compartment, said shaft being complementary to said reel;
a first spring positioned in said interior space, said first spring being clock-type, said first spring being coupled by an inner end to said shaft; and
wherein said shaft is positioned in said compartment such that said shaft is positioned for coupling to said reel, wherein said first spring is positioned on said shaft such that said first spring is configured for compressing as said tube is extended from said compartment, such that said first spring is positioned for compelling rotation of said reel coincident with said shaft for retracting said tube into said compartment.

2. The device of claim 1, further including said door comprising a first section and a second section, said first section being positioned in and hingedly coupled to a respective side of said first housing, said second section being coupled to and extending perpendicularly from said first section into a top of said first housing.

3. The device of claim 1, further including a grasp coupled to said door, wherein said grasp is positioned on said door such that said grasp is configured for grasping is a hand of a user for opening and closing said door.

4. The device of claim 3, further including said grasp comprising a cutout positioned through said door adjacent to an edge of said door.

5. The device of claim 1, further including a pipe fluidically coupled to said oxygen supplier, said pipe extending from said oxygen supplier to said compartment, wherein said pipe is positioned on said oxygen supplier such that said pipe is positioned for fluidically coupling said tube to said oxygen supplier.

6. The device of claim 1, further comprising:
a ratchet wheel coupled to said shaft and positioned in said interior space, said ratchet wheel comprising a plurality of teeth;
a pawl hingedly coupled to said second housing and positioned in said interior space, said pawl being operationally coupled to said ratchet wheel;
a second spring coupled to and extending between an endpoint of said pawl and an outer endpoint of said first spring, said second spring being extension-type; and
wherein said second spring is positioned on said pawl such that said second spring is configured for extending coincident with compressing of said first spring and extending of said tube from said compartment, wherein said second spring is positioned for partially rebounding for compelling said pawl for coupling to said ratchet wheel such that said tube is fixedly extended from said compartment, and wherein said tube is configured for grasping and extending from said compartment such that said pawl is compelled for decoupling from said ratchet wheel wherein said first spring is positioned for compelling rotation of said reel coincident with said shaft for retracting said tube into said compartment.

7. The device of claim 1, further including:
a bar coupled to said shaft, said bar being positioned longitudinally on said shaft within said compartment;
a channel axially positioned through said reel, said channel being complementary to shaft and said bar;
a pair of pulleys rotationally coupled to said respective said panel such that said pulleys are positioned in said compartment proximate to said hole when said door is closed; and
wherein channel is positioned in said reel such that said channel is positioned for inserting said bar and said shaft for coupling said reel to said shaft, wherein said pulleys are positioned in said compartment such that said pulleys are positioned for rotationally coupling to said tube for guiding said tube as said tube is selectively extended from and retracted into said compartment.

8. The device of claim 1, further including a handle coupled to and selectively extensible from said first housing, said handle being positioned on a top of said first housing proximate to a back of said first housing.

9. The device of claim 1, further comprising:
a pair of rollers coupled to and extending from a bottom of said first housing, said rollers being positioned proximate to said back of said first housing, each said roller being positioned proximate to a respective corner of said bottom; and
a pair of legs coupled to and extending from said bottom of said first housing, said legs being positioned proximate to said back of said first housing, each said leg being positioned proximate to a respective corner of said bottom.

10. The device of claim 9, further including said rollers comprising castors.

11. The device of claim 9, further including said legs being dimensionally taller than said rollers such that said first housing is tilted.

12. The device of claim 1, further comprising:
a power module coupled to said first housing and positioned in said internal space, said power module being operationally coupled to said oxygen supplier;
a control panel coupled to said top of said first housing, said control panel being operationally coupled to said power module and said oxygen supplier; and wherein said control panel is positioned on said first housing such that said control panel is configured for entering commands for controlling a flow rate of oxygen from said oxygen supplier through said tube.

13. The device of claim 12, further including said power module comprising a cord, said cord being configured for coupling to a source of alternating current.

14. The device of claim 13, further including said cord being retractable into said internal space.

15. The device of claim 12, further including a display coupled to said top of said first housing, said display being operationally coupled to said power module and said control panel, wherein said display is positioned on said first housing such that said display is configured for presenting to a user the flow rate of the oxygen from said oxygen supplier through said tube.

16. An oxygen delivery device comprising:
a first housing defining an internal space;
an oxygen supplier positioned in said internal space;
a reel rotationally coupled to said first housing and positioned in said internal space, said reel being spring-loaded;
a door positioned in and hingedly coupled to said first housing proximate to said reel, wherein said door is positioned in said first housing such that said door is configured for opening for accessing said reel, said door comprising a first section and a second section, said first section being positioned in and hingedly coupled to a respective side of said first housing, said second section being coupled to and extending perpendicularly from said first section into a top of said first housing;
a hole positioned through said door;
a grasp coupled to said door, wherein said grasp is positioned on said door such that said grasp is configured for grasping is a hand of a user for opening and closing said door, said grasp comprising a cutout positioned through said door adjacent to an edge of said door;
a tube coiledly positioned around said reel, said tube having a first end fluidically coupled to said oxygen supplier, wherein said tube is positioned around said reel such that a second end of said tube is configured for selectively reversibly extending from said first housing through said hole positioning said second end for coupling to an oxygen supply interface;
a plurality of panels coupled to said first housing and positioned in said internal space defining a compartment, wherein said door is positioned in said first housing such that said door is configured for opening for accessing said compartment;
a pipe fluidically coupled to said oxygen supplier, said pipe extending from said oxygen supplier to said compartment, wherein said pipe is positioned on said oxygen supplier such that said pipe is positioned for fluidically coupling said tube to said oxygen supplier;
a second housing coupled to a respective said panel and positioned in said internal space, said second housing and said respective said panel defining an interior space;
a shaft rotationally coupled to said second housing, said shaft extending from said second housing through a penetration in said respective said panel into said compartment, said shaft being complementary to said reel, wherein said shaft is positioned in said compartment such that said shaft is positioned for coupling to said reel;

a first spring positioned in said interior space, said first spring being clock-type, said first spring being coupled by an inner end to said shaft, wherein said first spring is positioned on said shaft such that said first spring is configured for compressing as said tube is extended from said compartment, such that said first spring is positioned for compelling rotation of said reel coincident with said shaft for retracting said tube into said compartment;
a ratchet wheel coupled to said shaft and positioned in said interior space, said ratchet wheel comprising a plurality of teeth;
a pawl hingedly coupled to said second housing and positioned in said interior space, said pawl being operationally coupled to said ratchet wheel;
a second spring coupled to and extending between an endpoint of said pawl and an outer endpoint of said first spring, said second spring being extension-type, wherein said second spring is positioned on said pawl such that said second spring is configured for extending coincident with compressing of said first spring and extending of said tube from said compartment, wherein said second spring is positioned for partially rebounding for compelling said pawl for coupling to said ratchet wheel such that said tube is fixedly extended from said compartment, and wherein said tube is configured for grasping and extending from said compartment such that said pawl is compelled for decoupling from said ratchet wheel wherein said first spring is positioned for compelling rotation of said reel coincident with said shaft for retracting said tube into said compartment;
a bar coupled to said shaft, said bar being positioned longitudinally on said shaft within said compartment;
a channel axially positioned through said reel, said channel being complementary to shaft and said bar, wherein channel is positioned in said reel such that said channel is positioned for inserting said bar and said shaft for coupling said reel to said shaft;
a pair of pulleys rotationally coupled to said respective said panel such that said pulleys are positioned in said compartment proximate to said hole when said door is closed, wherein said pulleys are positioned in said compartment such that said pulleys are positioned for rotationally coupling to said tube for guiding said tube as said tube is selectively extended from and retracted into said compartment;
a handle coupled to and selectively extensible from said first housing, said handle being positioned on said top of said first housing proximate to a back of said first housing;
a pair of rollers coupled to and extending from a bottom of said first housing, said rollers being positioned proximate to said back of said first housing, each said roller being positioned proximate to a respective corner of said bottom, said rollers comprising castors;
a pair of legs coupled to and extending from said bottom of said first housing, said legs being positioned proximate to said back of said first housing, each said leg being positioned proximate to a respective corner of said bottom, said legs being dimensionally taller than said rollers such that said first housing is tilted;
a power module coupled to said first housing and positioned in said internal space, said power module being operationally coupled to said oxygen supplier, said power module comprising a cord, said cord being configured for coupling to a source of alternating current, said cord being retractable into said internal space;

a control panel coupled to said top of said first housing, said control panel being operationally coupled to said power module and said oxygen supplier, wherein said control panel is positioned on said first housing such that said control panel is configured for entering commands for controlling a flow rate of oxygen from said oxygen supplier through said tube;

a display coupled to said top of said first housing, said display being operationally coupled to said power module and said control panel, wherein said display is positioned on said first housing such that said display is configured for presenting to the user the flow rate of the oxygen from said oxygen supplier through said tube; and wherein said door is positioned in said first housing such that said door is configured for opening for accessing said compartment for installing and replacing said reel, wherein said pipe is positioned on said oxygen supplier such that said pipe is positioned for fluidically coupling said tube to said oxygen supplier, wherein said pulleys are positioned in said compartment such that said pulleys are positioned for rotationally coupling to said tube for guiding said tube as said tube is selectively extended from and retracted into said compartment, wherein said second spring is positioned on said pawl such that said second spring is configured for extending coincident with compressing of said first spring and extending of said tube from said compartment, wherein said second spring is positioned for partially rebounding for compelling said pawl for coupling to said ratchet wheel such that said tube is fixedly extended from said compartment positioning said second end of said tube for coupling to the oxygen supply interface, wherein said tube is configured for grasping and extending from said compartment such that said pawl is compelled for decoupling from said ratchet wheel wherein said first spring is positioned for compelling rotation of said reel coincident with said shaft for retracting said tube into said compartment, wherein said control panel is positioned on said first housing such that said control panel is configured for entering the commands for controlling the flow rate of the oxygen from said oxygen supplier through said tube, wherein said display is positioned on said first housing such that said display is configured for presenting to the user the flow rate of the oxygen from said oxygen supplier through said tube.

* * * * *